United States Patent [19]

Andrus et al.

[11] Patent Number: 4,565,808
[45] Date of Patent: Jan. 21, 1986

[54] 3-PHOSPHONATE CARBAPENEMS

[75] Inventors: W. Alexander Andrus, Fanwood; Burton G. Christensen, Cliffside Park; James V. Heck, Fanwood, all of N.J.

[73] Assignee: Merck & Co., Inc., Rahway, N.J.

[21] Appl. No.: 529,194

[22] Filed: Sep. 6, 1983

[51] Int. Cl.$^4$ ........................ A61K 31/675; C07P 9/65
[52] U.S. Cl. ................................ 514/80; 260/239 A; 260/245.2 T
[58] Field of Search ................. 424/272; 260/245.2 T; 546/272; 514/80

[56] References Cited
PUBLICATIONS

Mak et al., *Tetrahedron Letters*, vol. 24, pp. 347–350, (1983).

*Primary Examiner*—Mark L. Berch
*Attorney, Agent, or Firm*—Hesna J. Pfeiffer; R. M. Speer; R. J. North

[57] ABSTRACT

3-Phosphonate carbapenems of the Formula:

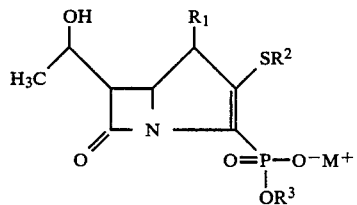

wherein $R^1$ is hydrogen, alkyl, amino, —NHCO-alkyl, hydroxy, alkoxy, halo, hydroxyalkyl, carboxyl or trifluoromethyl; $R^2$ is alkyl, substituted alkyl, heterocyclic or substituted heterocyclic; $R^3$ is hydrogen, alkyl or substituted alkyl; and M is a metal cation of $H^+$ are disclosed. The compounds are useful as antibiotics.

8 Claims, No Drawings

3-PHOSPHONATE CARBAPENEMS

BACKGROUND OF THE INVENTION

The present invention relates to 3-phosphonate carbapenems having a sulfur containing substituent. The carbapenems are useful as antibiotics.

Mak et al., *Tetrahedron Letters*, Vol. 24, pp. 347-350 (1983), attempted to prepare certain 3-phosphonate carbapenems having a sulfur containing substituent but failed.

There is a continuing need for new antibiotics. Unfortunately, continued wide-scale use of an antibiotic often gives rise to resistant strains of pathogens. In addition, the known antibiotics suffer from the disadvantage of being effective only against certain types of microorganisms. Accordingly, the search for new antibiotics continues.

The carbapenems of the present invention may be represented by the formula:

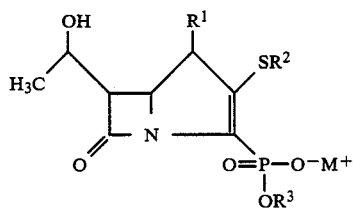

I wherein
$R^1$ is hydrogen, alkyl having 1 to 6 carbon atoms, amino, —NHCO-alkyl wherein the alkyl moiety has 1 to 6 carbon atoms, hydroxy, alkoxy wherein the alkyl moiety has 1 to 6 carbon atoms, halo (i.e., fluoro, chloro, bromo or iodo), hydroxyalkyl wherein the alkyl moiety has 1 to 6 carbon atoms, carboxyl or trifluoromethyl;
$R^2$ is alkyl having 1 to 6 carbon atoms, substituted alkyl wherein the alkyl moiety has 1 to 6 carbon atoms and is substituted with cyano, amino or

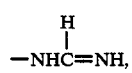

phenyl, phenyl substituted with at least one substituent wherein the substituents are selected from amino, —NHCOCH₃, —NHCH=NH, aminoalkyl wherein the alkyl moiety has 1 to 6 carbon atoms, nitro, halo (i.e. fluoro, chloro, bromo and iodo), alkyl having 1 to 6 carbon atoms and trifluoromethyl, pyrrolidinyl, N-substituted pyrrolidinyl wherein the substituent is selected from —CH=NH and

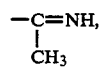

3-Δ'-2-amino-pyrrolidinyl, piperidinyl, 3-Δ'-2-amino-piperidinyl, and N,N-dimethylcarboxamidine; and
$R^3$ is hydrogen, a metal cation, alkyl having 1 to 6 carbon atoms, benzyl, substituted benzyl wherein the phenyl moiety of the benzyl group may be substituted with alkyl having 1 to 6 carbon atoms, chloro, fluoro or bromo,

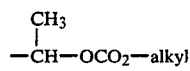

wherein the alkyl group has 1 to 6 carbon atoms,

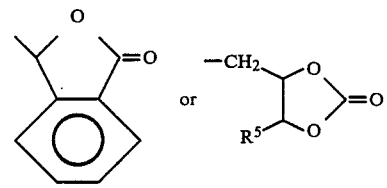

wherein the alkyl group has 1 to 6 carbon atoms,

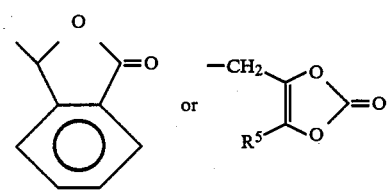

wherein $R^5$ is hydrogen or alkyl having 1 to 6 carbon atoms; and
M is a metal cation or H⁺.

Preferably, $R^1$ is hydrogen, methyl, ethyl, amino, —NHCOCH₃, hydroxyl, methoxy, ethoxy, fluoro, chloro, bromo, iodo, hydroxymethyl, carboxy or trifluoromethyl; $R^2$ is methyl, ethyl, cyanomethyl, cyanoethyl, aminoethyl, —CH₂CH₂NHCH=NH, phenyl substituted with at least one substituent wherein the substituents are selected from amino, —NHCOCH₃, —NHCH=NH, aminomethyl, nitro, halo, methyl, ethyl or trifluoromethyl, 3-pyrrolidinyl, 3-pyrrolidinyl substituted with —CH=NH or

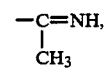

2-pyrrolidinyl, N-substituted 2-pyrrolidino wherein the substituent is —CH=NH or

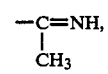

3-Δ¹-2-amino-pyrrolidinyl, 3-Δ¹-2-amino-piperidinyl, or N,N-dimethylcarboxamidine; and $R^3$ is hydrogen, a metal cation, methyl, ethyl, benzyl,

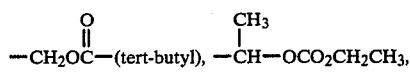

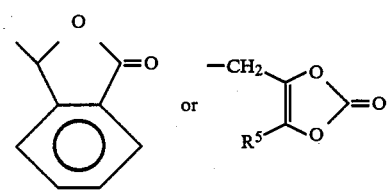

wherein $R^5$ is hydrogen, methyl, or tert-butyl, and M is a metal cation or H⁺.

Most preferably, $R^1$ is hydrogen, methyl, ethyl, amino, —NHCOCH₃, hydroxyl, methoxy, ethoxy, fluoro, chloro, bromo, iodo, hydroxymethyl, carboxy or trifluoromethyl; $R^2$ is cyanomethyl, cyanoethyl, 2- aminoethyl, —CH₂CH₂NHCH═NH, 3-pyrrolidinyl, 3-pyrrolidinyl substituted with —CH═NH or $$-\underset{\underset{CH_3}{|}}{C}=NH,$$

2-pyrrolidinyl, N-substituted 2-pyrrolidinyl wherein the substituent is —CH═NH or $$-\underset{\underset{CH_3}{|}}{C}=NH,$$

3-Δ¹-2-amino-pyrrolidinyl, 3-Δ¹-2-amino-piperidinyl, N,N-dimethylcarboxamidine, or phenyl substituted with a substituent selected from amino, —NHCOCH₃, —NHCH═NH, aminomethyl, nitro or halo; and R³ is hydrogen, a metal cation, methyl, ethyl, benzyl, methyl, ethyl, benzyl, $$-CH_2O\overset{O}{\underset{\|}{C}}-(tert\text{-}butyl) \text{ or } \underset{R^5}{\overset{-CH_2}{\underset{O}{\bigtriangleup}}}\!\!\!\!\!\!\!\!\overset{O}{\underset{O}{\diagdown}}\!\!\!\!=O$$

wherein R⁵ is hydrogen, methyl or tert-butyl and M is a metal cation or H⁺.

The aforementioned alkyl groups may have chain, branched and cyclic structures. Examples of alkyl groups are methyl, ethyl, propyl, isopropyl, butyl, tert-butyl, pentyl, hexyl and cyclohexyl.

The term metal cation is used herein means a pharmaceutically acceptable alkali or alkaline earth metal cation. Examples of such cations are sodium, potassium, calcium and magnesium. Preferably, M is sodium or potassium.

The present invention also relates to processes for the preparation of said carbapenems, pharmaceutical compositions comprising such compounds, and to methods of treatment comprising administering such compounds and compositions when an antibiotic effect is indicated.

The carbapenems of the present invention may have various optical isomers. Preferred isomers have the structure:

II wherein R¹, R², R³ and M⁺ are as defined above.

Illustrative examples of compounds of the present invention are the following:
sodium(5R,6S)-2-cyanomethylthio-6-(R-1-hydroxyethyl)-3-methylphosphonyl-carbapenem;
sodium(5R,6S)-2-phenylthio-6-(R-1-hydroxyethyl)-3-methylphosphonyl-carbapenem;
sodium(5R,6S)-2-(2-aminoethanethio)-6-(R-1-hydroxyethyl)-3-methylphosphonyl-carbapenem;
(5R,6S)-2-(2-formamidineethanethio)-6-(R-1-hydroxyethyl)-3-methylphosphonyl-carbapenem;
(5R,6S)-2-(2-aminoethanethio)-6-(R-1-hydroxyethyl)-3-benzylphosphonyl-carbapenem;
(5R,6S)-2-(2-aminoethanethio)-6-(R-1-hydroxyethyl)-3-phosphonyl-carbapenem;
(5R,6S)-2-N,N-dimethylcarbamimidoylmethylthio-6-(R-1-hydroxyethyl)-3-methylphosphonyl-carbapenem;
Potassium(5R,6S)-2-(2-cyanoethyl)thio-6-(R-1-hydroxyethyl)-3-methylphosphonyl-carbapenem;
(1R,5R,6S)-1-methyl-2-(2-aminoethanethio-6-(R-1-hydroxyethyl)-3-methylphosphonyl-carbapenem;
Potassium(1R,5R,6S)-1-trifluoromethyl-2-(2-acetamido)thio-6-(R-1-hydroxyethyl)-3-benzylphosphonyl-carbapenem;
Potassium(5R,6S)-2-ethylthio-6-(R-1-hydroxyethyl)-3-methylphosphonyl-carbapenem;
Potassium(5R,6S)-2-[(N-acetyl)aminoethylene]thio-6-(R-1-hydroxyethyl)-3-methylphosphonyl-carbapenem;
Potassium(5R,6S)-2-cyanomethylthio-6-(R-1-hydroxyethyl)-3-pivaloyloxymethylphosphonyl-carbapenem;
(1R,5R,6S)-1-amino-2-(3-S-(N-acetamidine)-pyrrolidinyl)thio-6-(R-1-hydroxyethyl)-3-methylphosphonyl-carbapenem;
sodium(5R,6S)-3-phenylthio-6-(R-1-hydroxyethyl)-1-azabicyclo[3.2.0]hept-2-en-7-one-2-dimethylphosphonate;
sodium(5R,6S)-3-cyanomethylthio-6-(R-1-hydroxyethyl)-1-azabicyclo[3.2.0]hept-2-en-7-one-2-methylphosphonate; and
potassium(5R,6S)-3-cyanomethylthio-6-(R-1-hydroxyethyl)-1-azabicyclo[3.2.0]hept-2-en-7-one-2-benzylphosphate.

The following are preferred compounds of the present invention:
sodium(5R,6S)-3-phenylthio-6-(R-1-hydroxyethyl)-1-azabicyclo[3.2.0]hept-2-en-7-one-2-dimethylphosphonate;
sodium(5R,6S)-3-cyanomethylthio-6-(R-1-hydroxyethyl)-1-azabicyclo[3.2.0.]hept-2-en-7-one-2-methylphosphonate; and
potassium(5R,6S)-3-cyanomethylthio-6-(R-1-hydroxyethyl)-1-azabicyclo[3.2.0]hept-2-en-7-one-2-benzylphosphonate.

The preparation of compounds of the present invention is illustrated by the following reaction scheme:

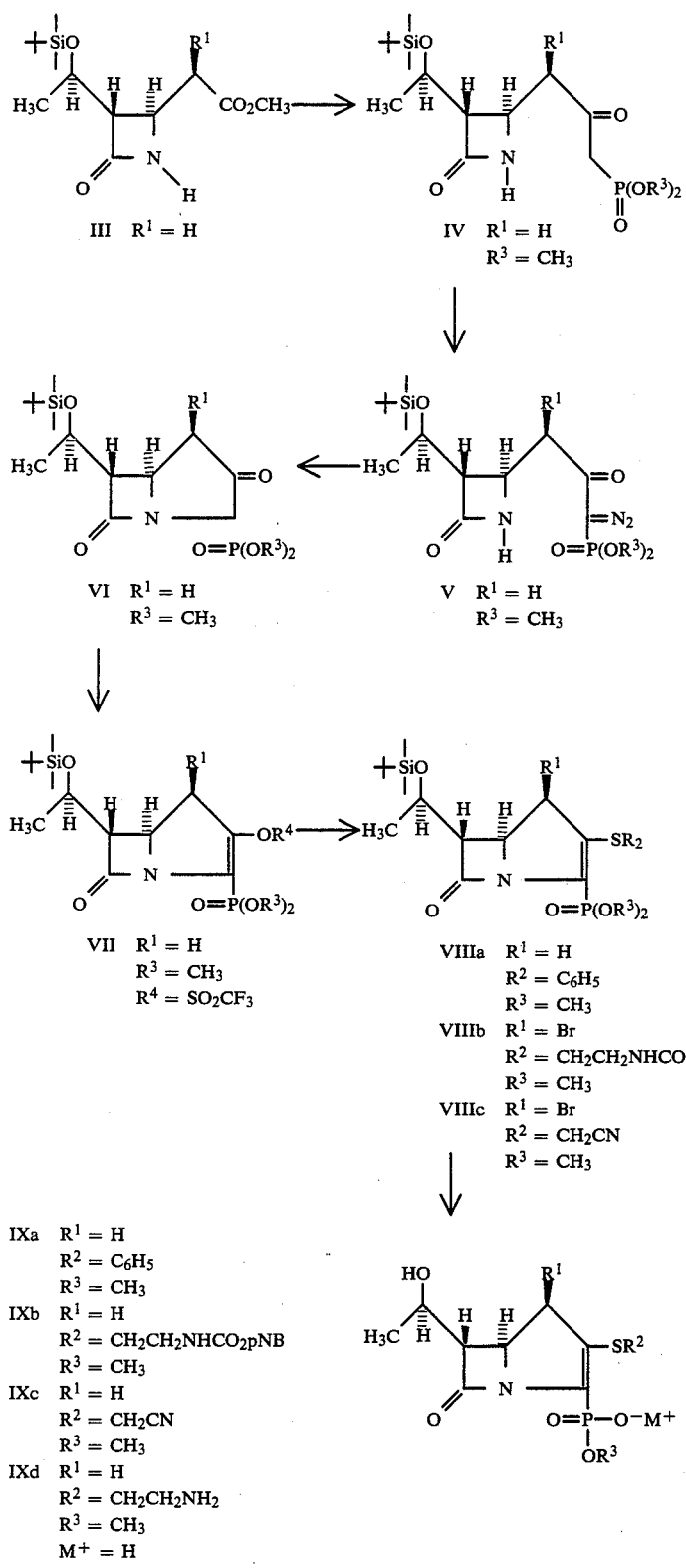

A chiral beta-lactam starting intermediate III, possessing all three asymmetric centers in the desired configuration is reacted with lithiomethyldimethylphosphonate to give the keto-phosphonate IV. This first reaction is the only carbon-carbon bond formation required. Diazo-transfer proceeds rapidly with p-dodecylbenzenesulfonylazide and diazobicycloundecene (DBU) as base to yield V. Refluxing V with a catalytic amount (about 1% by weight) of rhodium acetate dimer in dichloromethane gives pure VI after simple filtration. Triflation of the C-2 oxygen of VI with DBU and N-phenyltrifluoromethanesulfonimide or *freshly distilled* trifluoromethanesulfonic anhydride yields VII. Treatment of VII with thiophenol and N-p-nitrobenzyloxycarbonylcysteamine gives VIIIa and VIIIb. Addition of sodium hydrogen-sulfide to the triflate solution followed by chloroacetonitrile provides VIIIC. After desilylation, VIIIa-c are mono-demethylated with several equivalents of sodium iodide in acetone at reflux. Products IXa, IXb and IXc are isolated by reverse-phase preparative thin layer chromatography of the evaporated reaction mixture. Hydrogenation of IXb gives 3-methylphosphonyl thienamycin IXd.

Preparation of compounds of the present invention wherein $R^1$ is other than hydrogen is illustrated by the following reaction scheme:

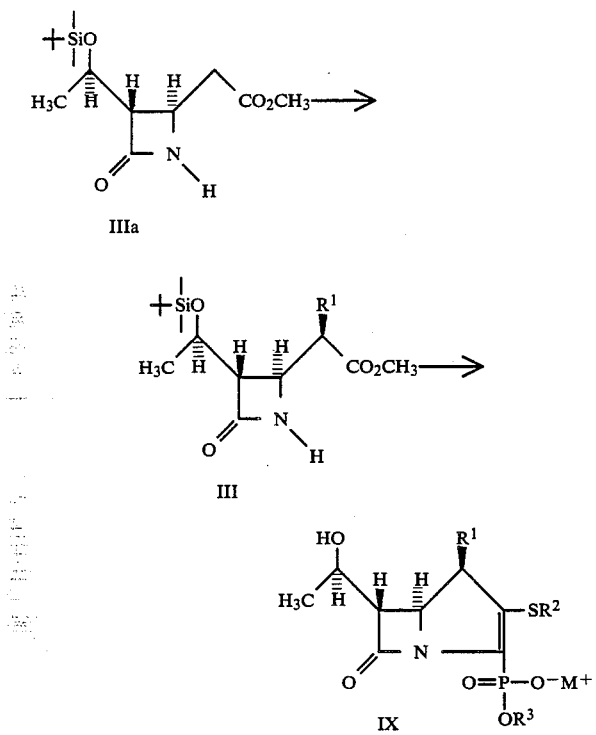

Compounds of the Formula III are prepared from compounds IIIa by an appropriate reaction. For example, IIIa is treated at low temperature in a solvent such as tetrahydrofuran, diethylether, or dioxane, with a strong base, such as lithium diisopropylamide, potassium tert-butoxide, or sodium hexamethyldisilazide, followed by an appropriate reagent such as methyl iodide ($R^1=CH_3$), bromine ($R^1=Br$) or carbon dioxide ($R^1=CO_2H$) to give the desired Compound III. Certain compounds of the Formula III can be used as intermediates in preparing other compounds. For example, Compound III where $R^1$ is bromine can be converted to the compound where $R^1$ is amino by reaction with sodium azide and dimethylformamide and reduction by hydrogenation.

The novel compounds are valuable antibiotics active against various gram-positive and gram-negative bacteria and, accordingly, find utility in human and veterinary medicine. The compounds of this invention may therefore be used as antibacterial drugs for treating infections caused by gram-positive or gram-negative bacteria, for example, against *Staphylococcus aureus*, *Escherichia coli*, *Klebsiella pneumoniae*, Serratia, *Pseudomonas aeruginosa*, Enterobacter, Enterococcus, and *Bacterium proteus*. The antibacterials of the invention may further be utilized as additives to animal feeds, for preserving foodstuffs and as disinfectants. For example, they may be employed in aqueous compositions in concentrations ranging from 0.1 to 100 parts of antibiotic per million parts of solution in order to destroy and inhibit one growth of harmful bacteria on medical and dental equipment and as bactericides in industrial applications, for example, in waterbased paints and in the white of paper mills to inhibit the growth of harmful bacteria.

The products of this invention may be used alone or in combination as an active ingredient in any one of a variety of pharmaceutical preparations. They may be combined with other drugs to provide compositions having a broad spectrum of activity. These antibiotics may be employed in capsule form or as tablets, powders or liquid solutions or as suspensions or elixirs. They may be administered orally, topically or parenterally by injection (intravenously or intramuscularly).

Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, cornstarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous of oily suspensions, solutions, emulsions, syrups, elixirs, etc. or may be presented as a dry product, for reconstitution with water or other suitable vehicles before use. Such liquid preparations may contain conventional additives such as suspending agents, for example, sorbitol, syrup, methyl cellulose, glycose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example, methyl or propyl p-hydroxybenzoates or sorbic acid. Suppositories will contain conventional suppository base, e.g. cocoa butter or other glyceride.

Compositions for injection may be presented in unit dose form in ampules, or in multidose containers with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long or quick-release bases.

The dosage to be administered depends to a large extent upon the condition and size of the subject being treated as well as the route and frequency of administration, the parenteral route being preferred for generalized infections and the oral route for intestinal infections. Another factor influencing the precise dosage regimen, apart from the nature of the infection and peculiar identity of the individual being treated, is the molecular weight of the chosen species of this invention. In general, a daily oral dosage consists of from about 2 to about 600 mg of active ingredient per kg of body weight of the subject in one or more applications per day. A preferred daily dosage for adult humans lies in the range of from about 15 to 150 mg of active ingredient per kg of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10 to 60%. The composition will generally contain from about 15 mg to about 1500 mg of the active ingredient; however, in general, it is preferable to employ a dosage amount in the range of from about 100 mg to 1000 mg. In parenteral administration the unit dosage is usually the pure compound in a sterile water solution or in the form of a soluble powder intended for solution. Consideration of individual properties of solubility and stability well determine the optimum pH of such a solution. The pH will generally be in range of 5.5 to 8.2.

The following Examples illustrate but do not limit the product, process, compositional or method of treatment aspect of the present invention. All temperatures are in °C.

EXAMPLE 1

Preparation of (3S,4R)-3-(R-2-(t-butyldimethylsilyloxy)ethyl)-4-(2-oxo-3-dimethylphosphonyl)propyl-azetidin-2-one (Compound 2)

A hexane solution of butyllithium (50 ml, 0.080 mol, 1.6M) was added by syringe to a −78° solution of dimethylmethylphosphonate (10.3 gm, 0.083 mol) and 250 ml dry, distilled tetrahydrofuran. After 15 minutes, a solution of (3S,4R)-3-(R-2-(t-butyldimethylsilyloxy)ethyl)-4-methylacetate-azetidin-2-one (Compound 1) (10.00 gm, 0.033 mol) in 50 ml tetrahydrofuran was transferred by cannula to the pale yellow, homogeneous solution. After one hour at −78°, the solution was allowed to warm to 0° and stir for 4 hours. The pH was adjusted to neutrality with 50 ml 10% sodium bisulfate. Most of the solvent was evaporated under vacuum. Dilution with ethyl acetate was followed by washing with water and saturated sodium chloride. the organic phase was dried over magnesium sulfate, filtered, and concentrated to induce crystallization. Two additional crops of crystals were obtained by crystallization from dichloromethane and hexane to yield 9.06 gm (70%) of Compound 2: m.p. 136° IR (CHCl$_3$) 3410, 1755, 1715 cm$^{-1}$, $^1$H nmr (CDCl$_3$)δ 6.06 (1H, br s); 4,18 (1H, m); 3.98 (1H, m); 3.77 (6H, d, J$_{HP}$=10); 3.12 (2H, d, J$_{HP}$=22); 2.8 (3H, m); 1.20 (3H, d, J=6); 0.87 (9H, s); 0.07 (6H, s); mass spec. 393 (M+), 336, 293, 292.

Anal: Calc.: C, 48.84; H, 8.20; N, 3.56 Found: C, 48.81; H, 8.23; N, 3.48.

[α]$_D^{25}$ = +18.4° (c=1, CH$_3$OH).

EXAMPLE 2

Preparation of (3S,4R)-3-(R-2-(t-butyldimethylsilyloxy)ethyl)-4-(2-oxo-3-diazo-3-dimethylphosphonyl)-propyl-azetidin-2-one (Compound 3)

A hexane solution of p-dodecylbenzenesulfonylazide (24 ml, 0.021 mol, 0.89 m) was added by syringe to a −15° solution of Compound 2 (6.85 gm, 0.017 mol) and 120 ml dichloromethane, followed by 1,8-diazabicyclo[5.4.0]undec-7-ene (2.9 ml, 0.019 mol). After one hour, the dark solution was diluted with dichloromethane and washed with solutions of 5% potassium dihydrogenphosphate and saturated sodium chloride. Drying over magnesium sulfate and filtration was followed by evaporation under vacuum and chromatography of the dark oil on silica gel. Elution gave 4.80 gm (66%) of Compound 3 as a yellow oil: IR (CHCl$_3$) 3410, 2120, 1755, 1645 cm$^{-1}$ $^1$H nmr (CDCl$_3$)δ 6.10 (1H, br s); 4.21 (1H, dd, J=56); 4.02 (1H, ddd, J=2.5, 3.5, 9.5); 3.88 (6H, d, J=13); 3.08 (1H, dd, J=3.5, 17.5); 2.85 (1H, dd, J=2.5, 5); 2.74 (1H, dd, J=9.5, 17.5); 1.24 (3H, d, J=6); 0.88 (9H, s); 0.08 (6H, s).

EXAMPLE 3

Preparation of (5R,6S)-3,7-dioxo-6-(R-1-t-butyldimethylsilyloxy)ethyl)-1-azabicyclo[3.2.0]heptane-(2S)-dimethylphosphonate (Compound 4)

A mixture of Compound 3 (4.80 gm, 0.0114 mol), rhodium acetate dimer (10 mg) and 200 ml dichloromethane were refluxed for six hours. After cooling to room temperature, the solution was filtered through a pad of magnesium sulfate. Evaporation and chromatography on silica gel gave 3.30 gm (74%) of Compound 4 as a white solid: m.p. 124°-25°.

IR (CHCl$_3$) 1760 cm$^{-1}$.

$^1$H NMR (CDCl$_3$)δ 4.47 (1H, d, J$_{HP}$=18.5); 4.32 (1H, dq, J=5,6); 4.19 (1H, ddd, J=2, 7, 7.5); 3.88 (3H, d, J=11); 3.85 (3H, d, J=11); 3.14 (1H, dd, J=2,5); 2.93 (1H, dd, J=7.5, 19); 2.39 (1H, dd, J=7, 19); 1.28 (1H, d, J=6); 0.90 (9H, s); 0.08 (6H, s).

[α]$_D^{25}$= +54.8° (c=1, CHCl$_3$).

EXAMPLE 4

Preparaton of (5R,6S)-3-(2-p-nitrobenzyloxycarbonyl)-aminoethanethio-6-(R-1-t-butyldimethylsilyloxy)ethyl-1-azabicyclo[3.2.0]hept-2-en-7-one-2-dimethylphosphonate (Compound 5)

N-phenyltrifluoromethanesulfonimide (0.160 gm, 0.45 mmol) was added to a solution of Compound 4 (0.146 gm, 0.37 mmol) and 6 ml dry tetrahydrofuran at −10°. 1,8-Diazabicyclo[5.4.0]undec-7-ene (0.067 ml, 0.45 mmol) was added. After 40 minutes, p-nitrobenzyloxycarbonylaminoethanethiol (0.115 gm, 0.45 mmol) and triethylamine (0.12 ml, 0.86 mmol) were added. The solution was allowed to warm to room temperature from −10° and stirred for 18 hours. Dilution with 100 ml ethyl acetate was followed by washing with 50 ml solutions of 5% potassium/dihydrogenphosphate, saturated sodium bicarbonate, and saturated sodium chloride. The organic phase was dried over magnesium sulfate, filtered, and evaporated to give a brown oil which was chromatographed on silica gel (ethyl acetate: hexane, 2:1) to give 0.047 gm (19%) of Compound 5 as an off-white solid: IR (CHCl$_3$) 1783, 1720 cm$^{-1}$ $^1$H nmr (CDCl$_3$)δ 8.26 (2H, d, J=8); 7.56 (2H, d, J=8); 6.80 (1H, br, N—H); 5.22 (2H, s); 4.26 (2H, m); 3.91 (3H, d, J=11); 3.89 (3H, d, J=11); 3.56 (2H, m); 2.76–3.36 (5H, m); 1.24 (3H, d, J=6); 0.88 (9H, s); 0.07 (3H, s); 0.06 (3H, s); UV (dioxane)λ$_{max}$; 280 nm.

EXAMPLE 5

Preparation of (5R,6S)-3-(2-p-nitrobenzyloxycarbonyl)-aminoethanethio-6-(R-1-hydroxyethyl)-1-azabicyclo[3.2.0-]hept-2-en-7-one-2-dimethylphosphonate (Compound 8)

Acetic acid (0.033 ml, 0.57 mmol) was added to a solution of Compound 5 (0.045 gm, 0.071 mmol) and 1.5 ml dry tetrahydrofuran at room temperature. After 3 minutes, tetra-n-butylammoniumfluoride (1M in tetrahydrofuran, 0.28 ml, 0.28 mmol) was added. The solution was stirred for 20 hours then diluted with 100 ml ethyl acetate and washed with 20 ml portions of 5% potassium dihydrogenphosphate, saturated sodium bicarbonate, and saturated sodium chloride. The organic phase was dried over magnesium sulfate, filtered, and evaporated to give 0.032 gm (87%) of Compound 8 as an off-white solid: IR (CHCl$_3$) 3690, 1780, 1722 cm$^{-1}$ $^1$H nmr (CDCl$_3$)δ 8.26 (2H, d, J=8); 7.58 (2H, d, J=8); 6.64 (1H, t, J=6); 5.24 (2H, s); 4.24 (2H, m); 3.91 (3H, d, J=11); 3.89 (3H, d, J=11); 2.8–3.55 (7H, m); 1.35 (2H, d, J=6); UVλ$_{max}$ 278 nm (dioxane).

EXAMPLE 6

Preparation of sodium (5R,6S)-3-(2-p-nitrobenzyloxycarbonyl)aminoethanethio-6-(R-1-hydroxyethyl)-1-azabicyclo[3.2.0-]hept-2-en-7-one-2-methylphosphonate (Compound 11)

Sodium iodide (0.058 gm, 0.39 mmol) was added to a solution of Compound 8 (0.040 gm, 0.078 mmol) and 4 ml acetone. The solution was heated to reflux for 2 hours, then solvent was removed under a stream of nitrogen with cooling to 0°. The residue was chromatographed (reverse phase silica gel prep TLC; 10% ethanol in water) to give 0.016 gm (39%) of Compound 11 as a white solid after lyophilization from water: $^1$H nmr (D$_2$O)δ 8.27 (2H, d, J=8; 7.60 (2H, d, J=8); 5.22 (2H, s); 4.1 (2H, m); 3.52 (3H, d, J=11); 2.8–3.4 (7H, m); 1.22 (3H, d, J=6). UVλ$_{max}$ 279 nm (H$_2$O).

EXAMPLE 7

Preparation of (5R,6S)-3-(2-aminoethanethio)-6-(R-1-hydroxyethyl)-1-azabicyclo[3.2.0]hept-2-en-7-one-2-methylphosphonate (Compound 13)

A mixture of Compound 11 (0.014 gm, 0.027 mmol), 28 mg 10% palladium on carbon, 1 ml ethanol, 1 ml tetrahydrofuran, and 1.5 ml 0.03M dipotassium hydrogenphosphate/potassium dihydrogenphosphate buffer was hydrogenated at 46 psi hydrogen for 1.5 hours. The mixture was filtered through diatomaceous earth (Celite), eluting with deionized water. The filtrate was washed with a 50 ml solution of 1:1/ethyl acetate:-diethyl ether and concentrated under vacuum. The residue was chromatographed (reverse phase silica gel prep TLC; 5% ethanol in water) to give 0.008 gm (95%) of Compound 13 as a white solid after lyophilization from water: $^1$H nmr (D$_2$O)δ 4.2 (2H, m); 3.58 (3H, d, J=11); 3.41 (1H, dd, J=2,6); 2.9–3.15 (m, 6H); 1.25 (3H, d, J=6); UVλ$_{max}$ 282 nm (H$_2$O).

EXAMPLE 8

Preparation of (5R,6S)-3-phenylthio-6-(R-1-t-butyldimethylsilyloxy)ethyl-1-azabicyclo[3.2.0]hept-2-en-7-one-2-dimethylphosphonate (Compound 7)

1,8-Diazabicyclo[5.4.0]undec-7-ene (0.75 ml, 5.0 mmol) was added to a solution of Compound 4 (1.63 gm, 4.17 mmol) and 50 ml dry tetrahydrofuran at −40°. After stirring 5 minutes, trifluoromethanesulfonic anhydride (0.76 ml, 4.5 mmol) was added. The solution was allowed to warm to −10° and stir for 2 hours. Thiophenol (0.51 ml, 4.9 mmol) and triethylamine (0.75 ml, 5.4 mmol) were added. The solution was allowed to warm to 0° and stir for 3 hours. Dilution with a solution of 150 ml ethyl acetate and 200 ml diethyl ether was followed by washing with 100 ml solutions of 5% potassium dihydrogenphosphate, saturated sodium bicarbonate, and saturated sodium chloride. The organic phase was dried over magnesium sulfate, filtered, evaporated and chromatographed on silica gel to give 0.477 gm (24%) of Compound 7 as a pale yellow oil: IR (CHCl$_3$) 1775 cm$^{-1}$ $^1$H nmr (CDCl$_3$)δ 7.56 (2H, m); 7.42 (3H, m); 4.2 (2H, m); 3.94 (3H, d, J=12); 3.90 (3H, d, J=12); 3.05 (1H, dd, J=3, 5); 2.69 (1H, dd, J=3, 9.5); 2.64 (1H, dd, J=3, 9.5); 1.17 (3H, d, J=6); 0.84 (9H, s); 0.03 (6H, s).

EXAMPLE 9

Preparation of (5R,6S)-3-cyanomethylthio-6-(R-1-t-butyldimethylsilyloxy)ethyl-1-azabicyclo[3.2.0]hept-2-en-7-one-2-dimethylphosphonate (Compound 6)

1,8-Diazabicyclo[5.4.0]undec-7-ene (0.14 ml, 0.92 mmol) was added to a solution of Compound 4 (0.299 gm, 0.76 mmol) and 12 ml tetrahydrofuran at −78°. After stirring 5 minutes, trifluoromethanesulfonic anhydride (0.15 ml, 0.92 mmol) was added. After one hour at −78°, the solution was warmed to 0° and solvent was removed under vacuum. The residue was cooled to −20° and 4 ml dry N,N-dimethylformamide was added, followed by sodium hydrogensulfide (0.051 gm, 0.92 mmol) and diisopropylethylamine (0.16 ml, 0.92 mmol). After 2.5 hours, chloroacetonitrile (0.18 ml, 2.8 mmol) and diisopropylethylamine (0.16 ml, 0.92 mmol) were added. The yellow solution was allowed to warm to room temperature and stir for 3 hours. Dilution with 150 ml ethyl acetate was followed by washing with 75 ml solutions of 5% potassium dihydrogenphosphate, saturated sodium bicarbonate, and saturated sodium chloride. The organic phase was dried over magnesium sulfate, filtered, evaporated, and chromatographed on silica gel to give 0.087 gm (26%) of Compound 6 as a clear oil: IR (CHCl$_3$) 1785 cm$^{-1}$ $^1$H nmr (CDCl$_3$)δ 4.35 (2H, m); 3.90 (3H, d, J$_{HP}$=11); 3.87 (3H, d, J$_{HP}$=11); 3.65 (2H, AB quartet, J=18); 3.28 (1H, ddd, J=2, 10, 17.5); 3.24 (1H, dd, J=3, 5); 3.19 (1H, ddd, J=4.5, 9, 17.5); 1.25 (3H, d, J=6); 0.88 (9H, s); 0.07 (6H, s); UVλ$_{max}$ (dioxane); 289 nm.

EXAMPLE 10

Preparation of (5R,6S)-3-cyanomethylthio-6-(R-1-hydroxyethyl)-1-azabicyclo[3.2.0]-hept-2-en-7-one-2-dimethylphosphonate (Compound 9)

Acetic acid (0.11 ml, 1.86 mmol) was added to a solution of Compound 6 (0.083 gm, 0.186 mmol) and 3 ml dry tetrahydrofuran at room temperature. After 5 minutes, tetra-n-butylammoniumfluoride (1M in tetrahydrofuran, 0.93 ml, 0.93 mmol) was added. The solution was stirred for 40 hours, then diluted with 150 ml ethyl acetate and washed with 30 ml portions of 5% potassium dihydrogenphosphate, saturated sodium bicarbonate, and saturated sodium chloride. The organic phase was dried over magnesium sulfate, filtered, and evaporated to give a brown oil. Chromatography on silica gel gave 0.009 gm (15%) of Compound 9 as a white solid: $^1$H nmr (CDCl$_3$)δ 4.25 (2H, m); 3.91 (3H, d, J=12); 3.88 (3H, d, J=12); 3.63 (2H, AB quartet, J=18); 3.37 (1H, ddd, J=2, 10, 18); 3.30 (1H, dd, J=3, 5); 3.18 (1H, ddd, J=4.5, 9, 18); 1.36 (3H, d, J=6); UVλ$_{max}$ 287 nm (dioxane).

EXAMPLE 11

Preparation of (5R,6S)-3-phenylthio-6-(R-1-hydroxyethyl)-1-azabicyclo[3.2.0]hept-2-en-7-one-2-dimethylphosphonate (Compound 10)

Acetic acid (0.45 ml, 7.9 mmol) was added to a solution of Compound 7 (0.477 gm, 0.99 mmol) and 15 ml dry tetrahydrofuran at room temperature. After 5 minutes, tetra-n-butylammonium fluoride (1M in tetrahydrofuran, 4.0 ml, 4 mmol) was added. The solution was stirred at room temperature for 30 hours an diluted with 250 ml ethyl acetate. The organic phase was washed with 100 ml portions of 5% potassium dihydrogenphosphate, saturated sodium bicarbonate, and saturated sodium chloride then dried over magnesium sulfate, filtered and evaporated under vacuum to give 0.376 gm (100% of Compound 10 as a brown oil: $^1$H nmr (CDCl$_3$)δ 7.58 (2H, m); 7.4 (3H, m); 4.2 (2H, m); 3.94 (3H, d, J=12); 3.90 (3H, d, J=12); 3.09 (1H, dd, J=3, 7); 2.72 (1H, d, J=9); 2.70 (1H, dd, J=1.5, 9); 1.30 (3H, d, J=6); UVλ$_{max}$ (dioxane) 295 nm.

EXAMPLE 12

Preparation of sodium (5R,6S)-3-phenylthio-6-(R-1-hydroxyethyl)-1-azabicyclo[3.2.0]hept-2-en-7-one-2-dimethylphosphonate (Compound 14)

Sodium iodide (0.24 gm, 1.6 mmol) was added to a solution of Compound 10 (0.147 gm, 0.40 mmol) and 10 ml acetone. The solution was heated to reflux for one hour. After solvent was removed under a stream of nitrogen at 0°, the residue was diluted with 20 ml water and washed with 20 ml diethyl ether. The aqueous phase was concentrated under vacuum and chromatographed (reverse phase silica gel prep TLC; 6% ethanol in water) to give 0.060 gm (40%) of Compound 14 as an off-white solid after lyophilization from water: $^1$H nmr (D$_2$O)δ 7.6 (2H, m); 7.5 (3H, m); 4.22 (1H, dq, J=5.5, 6); 4.16 (1H, dt, J=2.5, 9); 3.68 (3H, d, J$_{HP}$=12); 3.15 (1H, dd, J=2.5, 5.5); 2.76 (2H, m); 1.23 (3H, d, J=6); UVλ$_{max}$ (H$_2$O) 290 nm.

EXAMPLE 13

Preparation of sodium (5R,6S)-3-cyanomethylthio-6-(R-1-hydroxyethyl)-1-azabicyclo[3.2.0]hept-2-en-7-one-2-methylphosphonate (Compound 12)

Sodium iodide (0.032 gm, 0.22 mmol) was added to a solution of Compound 9 (0.009 gm, 0.027 mmol) and 3 ml acetone. The solution was heated to reflux for one hour. After solvent was removed under a stream of nitrogen at 0°, the residue was chromatographed (reverse phase silica gel prep TLC; 4% ethanol in water) to give 0.006 mg (62%) of Compound 12 as a white solid after lyophilization from water: $^1$H nmr (D$_2$O)δ 4.3 (2H, m); 3.87 (2H, AB, quartet, J=17.5); 3.60 (3H, d, J$_{HP}$=11); 3.49 (1H, dd, J=2.5, 5.5); 3.35 (1H, ddd, J=1.5, 10, 17.5); 3.19 (1H, ddd, J=4, 9, 17.5); 1.32 (3H, d, J=6.5); UVλ$_{max}$ (D$_2$O); 284 nm.

EXAMPLE 14

Preparation of (3S,4R)-3-(R-2-(t-butyldimethylsilyloxy)ethyl)-4-(2-oxo-3-dibenzylphosphonyl)propylazetidin-2-one (Compound 15)

A hexane solution of butyllithium (22 ml, 0.035 mol, 1.6M) was added by syringe to a −78° solution of dibenzylmethylphosphonate (9.77 gm, 0.035 mol) and 200 ml dry, distilled tetrahydrofuran. After 15 minutes, a solution of Compound 1 (4.21 gm, 0.014 mol) in 40 ml tetrahydrofuran was added to the orange, homogeneous solution. After two hours at −78°, the solution was allowed to warm to 0° and stir for three hours. The pH was adjusted to neutrality with 10% sodium bisulfate. Most of the solvent was evaporated under vacuum. Dilution with ethyl acetate was followed by washing with saturated sodium bicarbonate and sodium chloride solutions. The organic phase was dried over magnesium sulfate, filtered, and concentrated under vacuum. Chromatography on silica gel gave 4.06 gm (53%) of Compound 15 as a clear oil: IR (CHCl$_3$) 3410, 1755, 1715, 1495, 1455, 1375, 1310, 1250, 1020 cm$^{-1}$. $^1$H nmr (CDCl$_3$)δ 7.38 (10 H, br s); 5.93 (1H, br s) 5.95–6.15 (4H, m); 4.17 (1H, m); 3.90 (1H, dt, J=3, 10); 3.07 (2H, m, J$_{HP}$=23); 2.76–2.90 (2H, m); 2.65 (1H, dd, J=3, 5.5); 1.17 (3H, d, J=7); 0.86 (9H, s); 0.05 (3H, s); 0.04 (3H, s).

EXAMPLE 15

Preparation of (3S,4R)-3-(R-2-(t-butyldimethylsilyloxy)ethyl)-4-(2-oxo-3-diazo-3-dibenzylphosphonyl)-propyl-azetidin-2-one (Compound 16)

A hexane solution of p-dodecylbenzenesulfonylazide (4.9 ml, 4.4 mmol, 0.89M in hexane) was added by syringe to a −15° solution of Compound 15 (1.98 gm, 3.63 mmol) and 100 ml dichloromethane, followed by 1,8-diazabicyclo[5.4.0]undec-7-ene (0.60 ml, 4.0 mmol). After one hour, the yellow solution was diluted with 250 ml ethyl acetate and washed with solutions of 10% potassium bisulfate, saturated sodium bicarbonate, and saturated sodium chloride. Drying over magnesium sulfate and filtration was followed by evaporation under vacuum and chromatography of the dark oil on silica gel. Elution gave 1.48 g (71%) of Compound 16 as a yellow semi-solid: IR (CHCl$_3$) 3410, 2120, 1765, 1650, 1265, cm$^{-1}$. $^1$H nmr (CDCl$_3$)δ 7.42 (10H, br s); 5.86 (1H, br s); 5.16 (4H, d, J$_{HP}$=11); 4.16 (1H, m); 3.87 (1H, dt, J=3, 9); 2.85 (1H, dd, J=3.5, 17.5); 2.65 (1H, dd, J=2.5, 5); 2.49 (1H, dd, J=10, 17.5); 1.13 (3H, d, J=6); 0.85 (9H, s); 0.05 (6H, s).

EXAMPLE 16

Preparation of (5R,6S)-3,7-dioxo-6-(R-1-t-butyldimethylsilyloxy)ethyl-1-azabicyclo[3.2.0]heptane-(2S)-dibenzylphosphonate (Compound 17)

A mixture of Compound 16 (1.30 gm, 2.28 mmol), rhodium acetate dimer (5 mg) and 80 ml dichloromethane were refluxed for three hours. After cooling to room temperature, the solution was filtered through a pad of magnesium sulfate. Evaporation and chromatography on silica gel gave 0.92 g (74%) of Compound 17 as a pale yellow oil: IR (CHCl$_3$) 1770, 1260 cm$^{-1}$. $^1$H nmr (CDCl$_3$)δ 7.40 (10H, br s); 5.10 (4H, m); 4.48 (1H, d, J$_{HP}$=18.5); 4.16 (1H, m); 4.07 (1H, dt, J=2, 7); 3.11 (1H, dd, J=2, 5.5); 2.81 (1H, dd, J=7, 19.5); 2.37 (1H, dd, J=7, 19.5); 1.25 (3H, d, J=6); 0.86 (9H, s); 0.07 (3H, s); 0.04 (3H, s).

EXAMPLE 17

Preparation of (5R,6S)-3-cyanomethylthio-6-(R-1-t-butyldimethylsilyloxy)ethyl-1-azabicyclo[3.2.0]hept-2-en-7-one-2-dibenzylphosphonate (Compound 18)

1,8-Diazabicyclo[5.4.0]undec-7-ene (0.26 ml, 1.72 mmol) was added to a solution of Compound 17 (0.77 gm, 1.43 mmol), N-phenyltrifluoromethanesulfonimide (0.61 g, 1.72 mmol), and 25 ml dry, distilled tetrahydrofuran at −15°. After stirring one hour, most of the volatiles were removed under vacuum at 0°. The residue was cooled to 0° and sodium hydrogensulfide (0.096 gm, 1.72 mmol) in 20 ml dry N,N-dimethylformamide was added by syringe, followed by diisopropylethylamine (0.30 ml, 1.72 mmol). After 2 hours at 0°, chloroacetonitrile (0.27 ml, 4.3 mmol) and diisopropylethylamine (0.30 ml, 1.72 mmol) were added. The yellow solution was allowed to warm to room temperature and stir for 16 hours. Dilution with 250 ml ethyl acetate was followed by washing with solutions of 5% potassium dihydrogen phosphate, saturated sodium bicarbonate, and saturated sodium chloride. The organic phase was dried over magnesium sulfate, filtered, evaporated under vacuum, and chromatographed on silica gel to give 0.223 gm (26%) of Compound 18 as a clear oil: IR (CHCl$_3$) 1780 cm$^{-1}$; $^1$H nmr (CDCl$_3$)δ 7.38 (10H, m); 5.20 (4H, m); 4.22 (2H, m); 3.58 (1H, d, J=17); 3.46 (1H, d, J=17); 3.10 (3H, m); 1.27 (3H, d, J=6); 0.86 (9H, s); 0.08 (3H, s); 0.06 (3H, s).

UVλ$_{max}$ (dioxane) 289 nm.

EXAMPLE 18

Preparation of (5R,6S)-3-cyanomethylthio-6-(R-1-hydroxyethyl)-1-azabicyclo[3.2.0]hept-2-en-7-one-2-dibenzylphosphonate (Compound 19)

Acetic acid (0.26 ml, 4.5 mmol) was added to a solution of Compound 18 (0.223 gm, 0.37 mmol) and 8 ml dry, distilled tetrahydrofuran at room temperature. After 5 minutes, tetra-n-butylammonium fluoride (1M in tetrahydrofuran, 2.2 ml, 2.2 mmol) was added. The solution was stirred for 20 hours, then diluted with 250 ml ethylacetate and washed with solutions of 5% potassium dihydrogenphosphate, saturated sodium bicarbonate, and saturated sodium chloride. The organic phase was dried over magnesium sulfate, filtered, and evaporated under vacuum. The dark oil was chromatographed on silica gel to give 0.59 gm (33%) of Compound 19 as a white solid: $^1$H nmr (CDCl$_3$)δ 3.9 (10H, m); 5.20 (2H, d, J$_{HP}$=11); 5.16 (2H, d, J$_{HP}$=11); 4.20 (2H, m); 3.55 (1H, d, J=17); 3.41 (1H, d, J=17); 3.23 (1H, dd, J-3, 6.5); 3.21 (1H, ddd, J=2, 9, 17); 3.06 (1H, ddd, J=4.5, 9, 17); 1.32 (3H, d, J=6.5).

UVλ$_{max}$ (dioxane) 288 nm.

EXAMPLE 19

Preparation of Potassium (5R,6S)-3-cyanomethylthio-6-(R-1-hydroxyethyl)-1-azabicyclo[3.2.0]hept-2-en-7-one-2-benzylphosphonate (Compound 20)

A mixture of Compound 19 (0.028 gm, 0.058 mmol), 60 mg 10% palladium on carbon, 2 ml ethanol, 2 ml tetrahydrofuran, and 2 ml 0.03M dipotassium hydrogen phosphate/potassium dihydrogenphosphate pH 7 buffer was hydrogenated at 47 psi hydrogen for 3 hours. The mixture was filtered through diatomaceous earth, eluting with distilled water. The filtrate was washed with a 40 ml solution of 1:1/ethyl acetate:diethyl ether and concentrated under vacuum to a volume of 1 ml, which was chromatographed (reverse phase silica gel preparative tlc; 10% ethanol in water) to give a single band. Elution of the reverse phase silica gel with 30 ml of a 4:1/acetonitrile:water mixture was followed by concentration under vacuum to a 2 ml volume and then lyophilization to give 0.014 g (55%) of Compound 20 as a white solid: $^1$H nmr (D$_2$O)δ 7.40 (5H, br s); 4.95 (2H, d, J$_{HP}$=9); 4.10 (2H, m); 3.80 (1H, d, J=17); 3.69 (1H, d, J=17); 3.33 (1H, dd, J=2.5, 6); 3.10 (2H, m); 1.24 (3H, d, J=6).

EXAMPLE 20

Preparation of Pharmaceutical Compositions

One such unit dosage form consists in mixing 120 mg of sodium (5R,6S)-3-phenylthio-6-(R-1-hydroxyethyl)-1-azabicyclo[3.2.0]hept-2-en-7-one-2-dimethylphosphonate (product of Example 12) with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules and should it be necessary to mix more than 145 mg of ingredients together, larger capsules or as compressed tablets and pills can also be prepared. The following examples are illustrative of the preparation of pharmaceutical formulations:

| TABLET | Per Tablet |
| --- | --- |
| sodium (5R,6S)-3-phenylthio-6-(R—1-hydroxyethyl)-1-azabicyclo[3.2.0]hept-2-en-7-one-2-dimethylphosphonate | 125 mg |
| Cornstarch, U.S.P. | 6 mg |
| Dicalcium Phosphate | 192 mg |
| Lactose, U.S.P. | 190 mg |
| Magnesium Stearate | 287 mg |

The active ingredient is blended with the dicalcium phosphate, lactose and about half of the cornstarch. The mixture is then granulated with a 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter, each weighing 800 mg.

| PARENTERAL SOLUTION Ampoule: | |
|---|---|
| sodium (5R,6S)-3-phenylthio-6-(R—1-hydroxyethyl)-1-azabicyclo[3.2.0]hept-2-en-7-one-2-dimethylphosphonate | 500 mg |
| Sterile water | 2 ml |
| OPHTHALMIC SOLUTION | |
| sodium (5R,6S)-3-phenylthio-6-(R—1-hydroxyethyl)-1-azabicyclo[3.2.0]hept-2-en-7-one-2-dimethylphosphonate | 100 mg |
| Hydroxypropylmethylcellulose | 5 mg |
| Sterile water to | 1 ml |
| OTIC SOLUTION | |
| sodium (5R,6S)-3-phenylthio-6-(R—1-hydroxyethyl)-1-azabicyclo[3.2.0]hept-2-en-7-one-2-dimethylphosphonate | 100 mg |
| Benzalkonium Chloride | 0.1 mg |
| Sterile water to | 1 ml |
| TOPICAL OINTMENT | |
| sodium (5R,6S)-3-phenylthio-6-(R—1-hydroxyethyl)-1-azabicyclo[3.2.0]hept-2-en-7-one-2-dimethylphosphonate | 100 mg |
| Polyethylene Glycol 4000 U.S.P. | 400 mg |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound of the formula:

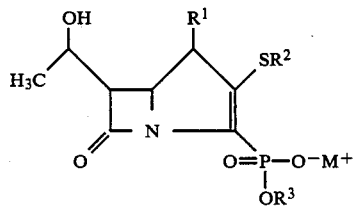

I wherein $R^1$ is hydrogen, alkyl having 1 to 6 carbon atoms, amino, —NHCO-alkyl wherein the alkyl moiety has 1 to 6 carbon atoms, hydroxy, alkoxy wherein the alkyl moiety has 1 to 6 carbon atoms, halo, hydroxyalkyl wherein the alkyl moiety has 1 to 6 carbon atoms, carboxyl or trifluoromethyl;

$R^2$ is alkyl having 1 to 6 carbon atoms, substituted alkyl wherein the alkyl moiety has 1 to 6 carbon atoms and is substituted with cyano, amino or

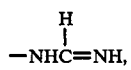

phenyl, phenyl substituted with at least one substituent wherein the substituents are selected from amino, —NHCOCH₃, —NHCH═NH, aminoalkyl wherein the alkyl moiety has 1 to 6 carbon atoms, nitro, halo, alkyl having 1 to 6 carbon atoms and trifluoromethyl, pyrrolidinyl, N-substituted pyrrolidinyl wherein the substituent is selected from —CH═NH and

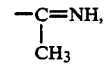

3-$\Delta^1$-2-amino-pyrrolidinyl, piperidinyl, 3-$\Delta^1$-2-amino-piperidinyl, and N,N-dimethylcarboxamidine; and $R^3$ is hydrogen, a metal cation, alkyl having 1 to 6 carbon atoms, benzyl, substituted benzyl wherein the phenyl moiety of the benzyl group may be substituted with alkyl having 1 to 6 carbon atoms, chloro, fluoro or bromo,

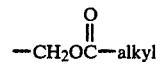

wherein the alkyl group has 1 to 6 carbon atoms,

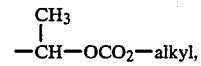

wherein the alkyl group has 1 to 6 carbon atoms,

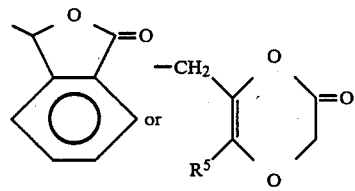

wherein $R^5$ is hydrogen or alkyl having 1 to 6 carbon atoms; and

M is a metal cation or H⁺.

2. A compound according to claim 1 wherein $R^1$ is hydrogen, methyl, ethyl, amino, —NHCOCH₃, hydroxyl, methoxy, ethoxy, fluoro, chloro, bromo, iodo, hydroxymethyl, carboxy or trifluoromethyl; $R^2$ is methyl, ethyl, cyanomethyl, cyanoethyl, aminoethyl, —CH₂CH₂NHCH═NH, phenyl substituted with at least one substituent wherein the substituents are selected from amino, —NHCOCH₃, —NHCH═NH, aminomethyl, nitro, halo, methyl, ethyl or trifluoromethyl, 3-pyrrolidinyl, 3-pyrrolidinyl substituted with —CH═NH or

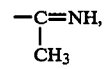

2-pyrrolidinyl, N-substituted 2-pyrrolidino wherein the substituent is —CH═NH or

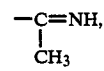

3-$\Delta^1$-2-amino-pyrrolidinyl, 3-$\Delta^1$-2-amino-piperidinyl, or N,N-dimethylcarboxamidine; and $R^3$ is hydrogen, a metal cation, methyl, ethyl, benzyl,

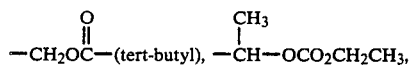

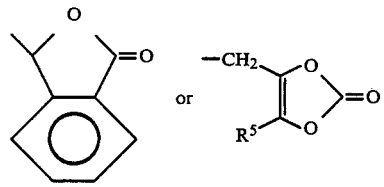

wherein $R^5$ is hydrogen, methyl, or tert-butyl, and M is a metal cation or $H^+$.

3. A compound according to claim 1, wherein $R^1$ is hydrogen, methyl, ethyl, amino, —NHCOCH$_3$, hydroxyl, methoxy, ethoxy, fluoro, chloro, bromo, iodo, hydroxymethyl, carboxy or trifluoromethyl; $R^2$ is cyanomethyl, cyanoethyl, 2-aminoethyl, —CH$_2$CH$_2$NHCH=NH, 3-pyrrolidinyl, 3-pyrrolidinyl substituted with —CH=NH or

2-pyrrolidinyl, N-substituted 2-pyrrolidinyl wherein the substituent is —CH=NH or

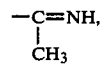

3-Δ$^1$-2-amino-pyrrolidinyl, 3-Δ$^1$-2-amino-piperidinyl, N,N-dimethylcarboxamidine, or phenyl substituted with a substituent selected from amino, —NHCOCH$_3$, —NHCH=NH, aminomethyl, nitro or halo; and $R^3$ is hydrogen, a metal cation, methyl, ethyl, benzyl,

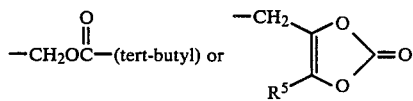

wherein $R^5$ is hydrogen, methyl or tert-butyl and M is a metal cation or $H^+$.

4. Sodium (5R,6S)-3-phenylthio-6-(R-1-hydroxyethyl)-1-azabicyclo[3.2.0]hept-2-en-7-one-2-dimethylphosphonate, according to claim 1.

5. Sodium (5R,6S)-3-cyanomethylthio-6-(R-1-hydroxyethyl)-1-azabicyclo[3.2.0]hept-2-en-7-one-2-methylphosphonate, according to claim 1.

6. Potassium (5R,6S)-3-cyanomethylthio-6-(R-1-hydroxyethyl)-1-azabicyclo[3.2.0]hept-2-en-7-one-2-benzylphosphonate, according to claim 1.

7. An antibacterial pharmaceutical composition comprising an effective amount of a compound of claim 1 and a pharmaceutically acceptable carrier.

8. A method of treating a bacterial infection in mammals comprising administering to a mammal in need of such treatment an antibacterially effective amount of an antibacterial pharmaceutical composition according to claim 7.

* * * * *